(12) United States Patent
Guler et al.

(10) Patent No.: US 11,656,529 B2
(45) Date of Patent: May 23, 2023

(54) LIGHT CONVERSION SYSTEMS, METHODS, AND DEVICES

(71) Applicant: Goodrich Lighting Systems, Inc., Phoenix, AZ (US)

(72) Inventors: Urcan Guler, Avon, CT (US); Matthew R. Pearson, Hartford, CT (US); Joseph V. Mantese, Ellington, CT (US)

(73) Assignee: Goodrich Lighting Systems, Inc., Phoenix, AZ (US)

( * ) Notice: Subject to any disclaimer, the term of this patent is extended or adjusted under 35 U.S.C. 154(b) by 0 days.

(21) Appl. No.: 17/406,950

(22) Filed: Aug. 19, 2021

(65) Prior Publication Data
US 2023/0056431 A1    Feb. 23, 2023

(51) Int. Cl.
*G02F 1/39*    (2006.01)
*G02F 1/35*    (2006.01)
*A61L 2/08*    (2006.01)

(52) U.S. Cl.
CPC ............ *G02F 1/397* (2013.01); *G02F 1/3507* (2021.01); *A61L 2/08* (2013.01)

(58) Field of Classification Search
CPC ................................ G02F 1/3619; G02F 1/397
See application file for complete search history.

(56) References Cited

U.S. PATENT DOCUMENTS

| | | | | |
|---|---|---|---|---|
| 6,396,617 B1 * | 5/2002 | Scalora | ................ | G02B 6/1225 385/5 |
| 6,414,780 B1 * | 7/2002 | D'Aguanno | ........... | B82Y 20/00 385/5 |
| 6,538,794 B1 * | 3/2003 | D'Aguanno | .............. | G02F 1/37 359/260 |
| 7,760,053 B2 * | 7/2010 | Kochergin | ........... | G02B 6/1225 333/208 |

(Continued)

FOREIGN PATENT DOCUMENTS

| | | |
|---|---|---|
| EP | 2302449 | 3/2011 |
| EP | 3861404 | 8/2021 |

OTHER PUBLICATIONS

Kavita Devi, et al., "Continuous-wave, single-pass, single-frequency second-harmonic-generation at 266 nm based on birefringent-multicrystal scheme", ICFO—Institut de Ciencies Fotoniques, Barcelona Institute of Science and Technology, 08860 Castelldefels (Barcelona), Spain, published Apr. 13, 2016, pp. 1-13, vol. 24, No. 8 | DOI:10.1364/OE.24.008763 | Optics Express 8763.

(Continued)

*Primary Examiner* — Rhonda S Peace
(74) *Attorney, Agent, or Firm* — Snell & Wilmer L.L.P.

(57) ABSTRACT

A nonlinear converter may comprise: alternating layers of a dielectric material and a metal material; a first refractive index of the nonlinear converter for a first wavelength (i.e., input wavelength or pump wavelength) between 207 nm and 237 nm, the first refractive index being less than 0.5, the first refractive index corresponding to metal fill ratio; and a (Continued)

second refractive index of the nonlinear converter for a second wavelength (i.e., output wavelength or SHG wavelength), the second wavelength being approximately double the first wavelength, the second refractive index corresponding to the metal fill ratio.

16 Claims, 9 Drawing Sheets

(56) References Cited

U.S. PATENT DOCUMENTS

| | | | |
|---|---|---|---|
| 9,550,005 | B2 | 1/2017 | Lin et al. |
| 10,307,495 | B2* | 6/2019 | Mori ........................ A61N 5/06 |
| 10,866,484 | B2 | 12/2020 | Lin et al. |
| 2014/0105784 | A1 | 4/2014 | Smeeton et al. |
| 2017/0290932 | A1 | 10/2017 | Mori et al. |
| 2022/0011646 | A1* | 1/2022 | Semmlinger ........... G02F 1/354 |

OTHER PUBLICATIONS

Haim Suchowski, et al., "Phase Mismatch-Free Nonlinear Propagation in Optical Zero-Index Materials", Sciencemag.org, published Dec. 6, 2013, pp. 1223-1226, vol. 342.
European Patent Office, European Search Report dated Jan. 4, 2023 in Application No. 22189331.6.
Alexander K Popov, et al. "Merging Nonlinear Optics and Negative-Index Metamaterials", arxiv.org, Cornell University Library, dated Aug. 3, 2021, 27 pages.

* cited by examiner

LIGHT CONVERSION SYSTEMS, METHODS, AND DEVICES

FIELD

The present disclosure relates generally to sanitization systems and methods and, more particularly, to sanitization systems and method using frequency doubling to generate FAR-UVC for aircrafts.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A nonlinear converter is disclosed herein. The nonlinear converter may comprise: alternating layers of a dielectric material and a metal material, the nonlinear converter configured to receive a first wavelength and output a second wavelength; a first refractive index of the nonlinear converter for the first wavelength, the first wavelength being approximately double the second wavelength, the first refractive index corresponding to a metal fill ratio; and a second refractive index of the nonlinear converter for the second wavelength, the second wavelength being between 207 nm and 237 nm, the second refractive index being less than 0.5, the second refractive index corresponding to the metal fill ratio.

In various embodiments, at least a portion of the first wavelength is halved in response to traveling through the nonlinear converter. Approximately equal may be between 0% and 10% or between 0% and 5%. The dielectric material may be aluminum nitride, and the metal material may be aluminum. The second refractive index may be between 0 and 0.3. The nonlinear converter may be configured to receive a first light with the first wavelength and output the first light and a second light with the second wavelength.

A sanitization apparatus is disclosed herein. The sanitization apparatus may comprise: a light source configured to emit a light having a first wavelength between 414 and 474 nm; and a nonlinear converter disposed proximate to the light source, the nonlinear converter comprising alternating layers of a dielectric material and metal material, the nonlinear converter configured to provide a phase mismatch between an input wavelength and a second harmonic generation wavelength between 0% and 10% within the nonlinear converter.

In various embodiments, the second harmonic generation wavelength is between 207 and 237 nm. A first refractive index of the nonlinear converter for the second harmonic generation wavelength may be less than 0.5, the first refractive index corresponding to metal fill ratio of the alternating layers. In various embodiments, a second refractive index of the nonlinear converter for the input wavelength is approximately double the first wavelength. The second refractive index may correspond to the metal fill ratio. The nonlinear converter may be configured to generate a third wavelength and fourth wavelength within traveling through the alternating layers of the dielectric material and the metal material, the third wavelength and the fourth wavelength being approximately equal. Approximately equal may be between 0% and 5%.

A method of sanitizing a surface is disclosed herein. The method may comprise: generating a light having a first wavelength between 414 and 474 nm; and converting the light into a first portion of the light having the first wavelength and a second portion of the light having a second wavelength, the second wavelength being half the first wavelength, converting the light being through a phase-mismatch free medium, the phase-mismatch free medium including a phase mismatch between 0% and 10%.

In various embodiments, converting the light further comprising generating, via a nonlinear converter, a third wavelength corresponding to the first wavelength and a fourth wavelength corresponding to the second wavelength, the third wavelength and the fourth wavelength being approximately equal. The method may further comprise directing the second portion of the light towards the surface. Directing the second portion of the light toward the surface may be through a prism. The method may further comprise the first portion of the light in a first direction that is collimated with a second direction of the second portion of the light. The method may further comprise scanning a predetermined area of the surface with the second portion of the light.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1:
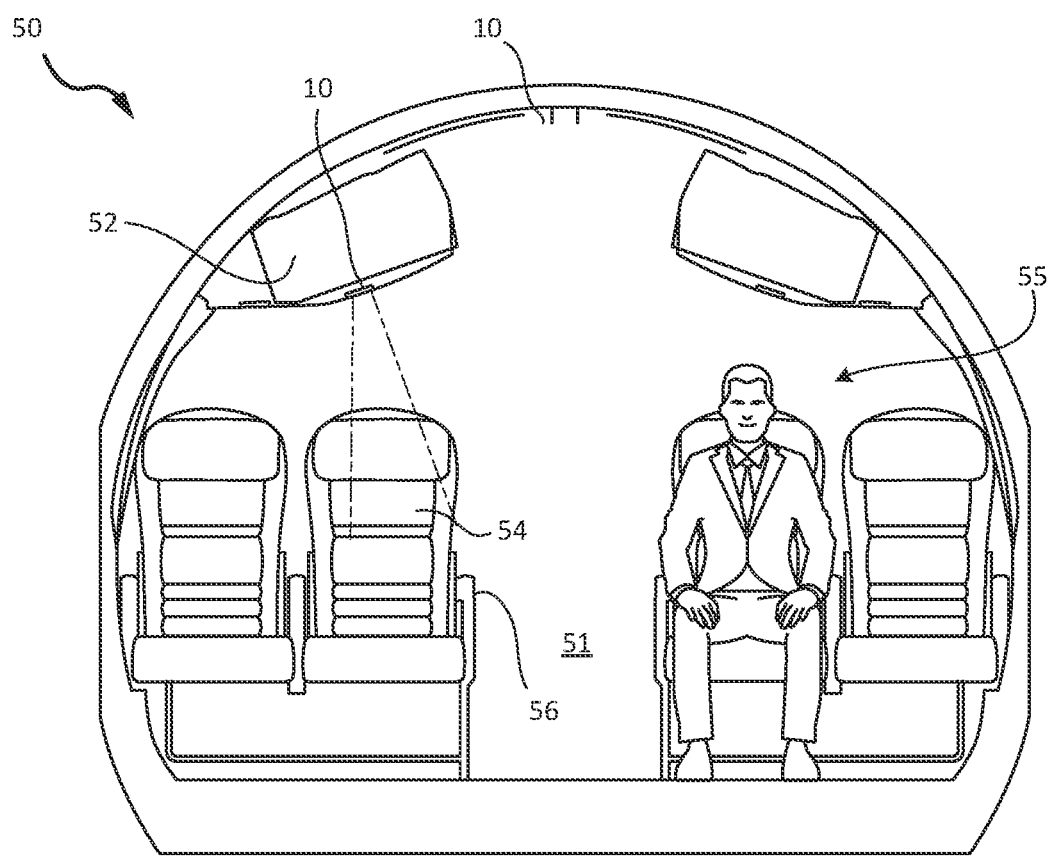
FIG. 1 illustrates a view of a cabin of an aircraft, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

In various embodiments, Far-UV (222 nm wavelength light) has promise to work in occupied spaces but may utilize significant power to disinfect an entirety of a cabin. Additionally, Far-UV (222 nm wavelength light) may have limitations as to total dosage a human may receive. In various embodiments, integrating Far-UV (222 nm wavelength light) via excimer lamps would be relatively expensive and utilize heavy high power intensity light sources, such as excimer lamps. Excimer lamps utilize a high voltage supply and have a large gas discharge. In various embodiments, the systems and methods disclosed herein are configured to generate a first light with a first wavelength (i.e., input wavelength or pump wavelength), convert a portion of the first light to a second light with a second wavelength (i.e., output wavelength or second harmonic generation (SHG) wavelength), the second wavelength (i.e., output wavelength or second harmonic generation (SHG) wavelength) being half the first wavelength (i.e., input wavelength or pump wavelength), and/or maintain a portion of the first light as an indicator. In various embodiments, the first wavelength (i.e., input wavelength or pump wavelength) is between 414 nm and 474 nm, or between 429 nm and 459 nm, or approximately 444 nm.

In various embodiments, the sanitization system disclosed herein, utilize an improved light converter. The improved light converter disclosed herein may replace conventional phase-matching techniques, while maintaining a frequency doubling/wavelength halving effect to facilitate conversion of blue light (between 414 and 474 nm) to at least a portion of Far-UV light (222 nm light).

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
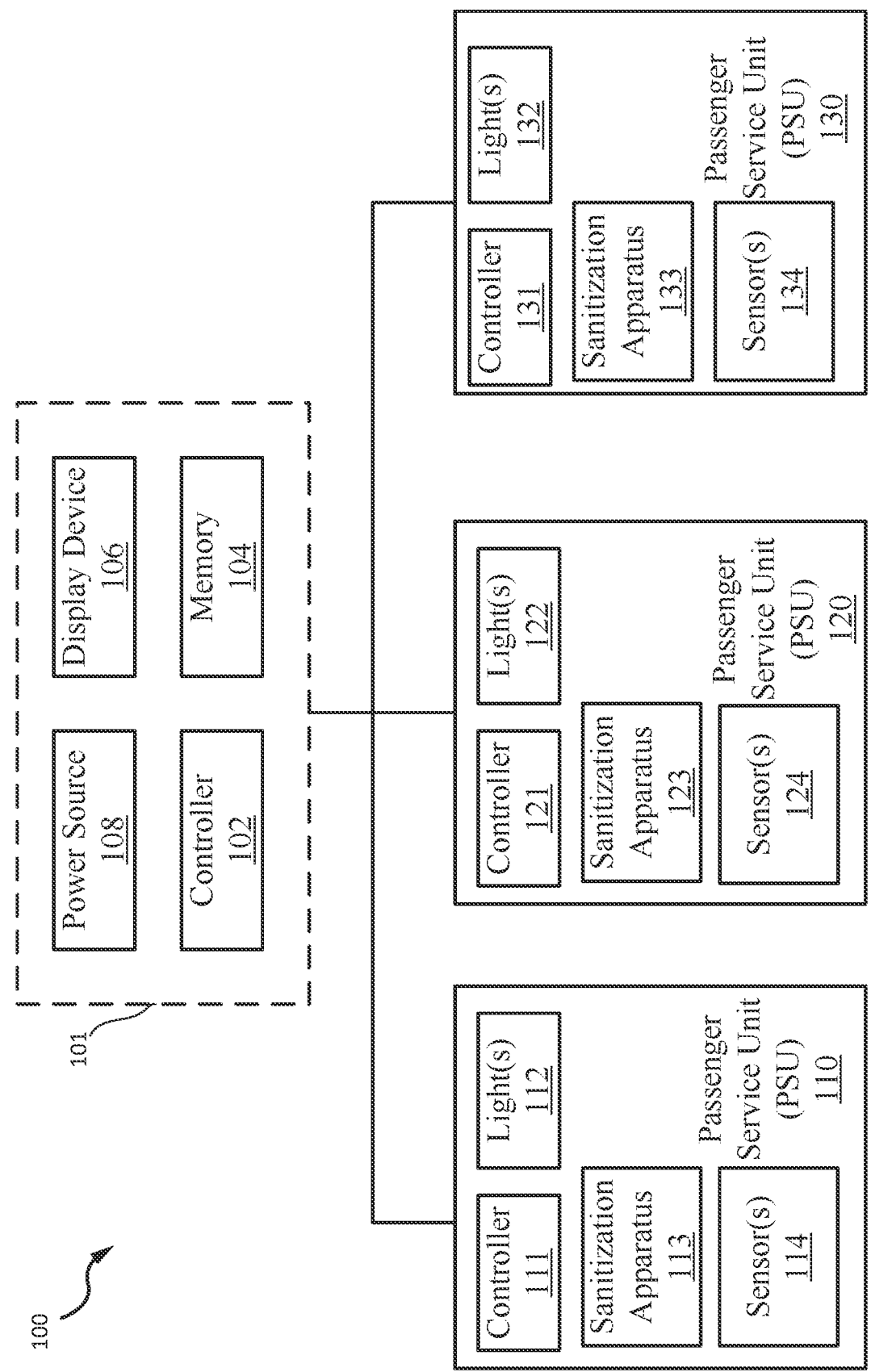
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory known in the art. The memory 104 may store instructions usable by the logic device to perform operations. Any appropriate computer-readable type/configuration may be utilized as the memory 104, any appropriate data storage architecture may be utilized by the memory 104, or both.

The database 104 may be integral to the control system 101 or may be located remote from the control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations, such as performing cleaning schedules between flights, cleaning a specific row in response to a trigger (i.e., a sneeze or the like), etc.

In various embodiments, the main control system 101 from FIG. 2 further comprises a power source 108 and a display device 106. The power source 108 may comprise any power source known in the art, such as a battery, a solar source, an alternating current (AC) source, a rechargeable source, or the like. In various embodiments, the display device 106 may be configured to provide inputs into the control system 101 and alternate between various modes (e.g., alternating from an in-flight mode to a post-flight mode or the like). In various embodiments, the sanitization system 100 may alternate modes automatically in response to detecting a change in mode is desired, as described further herein.

In various embodiments, the main control system 101 is in operable communication with each PSU in the plurality of PSUs (e.g., PSUs 110, 120, 130). In various embodiments, each PSU comprises a local controller (e.g., controllers 111, 121, 131). Each local controller (e.g., controllers 111, 121, 131) may be in accordance with main controller 102). For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory known in the art. The memory may store instructions usable by the logic device to perform operations. Any appropriate computer-readable type/configuration may be utilized as the memory, any appropriate data storage architecture may be utilized by the memory, or both.

In various embodiments, each PSU (e.g., PSUs 110, 120, 130) may comprise light(s) (e.g., light(s) 112, 122, 132), a sanitization apparatus (e.g., sanitization apparatus 113, 123, 133), and/or sensor(s) (e.g., sensors 114, 124, 134). As described further herein, the controller 102 may command the various local controllers (e.g., controllers 111, 121, 131) to instruct the devices therein.

In various embodiments, the power source 108 is sized and configured to power all of the lights (e.g., light(s) 112, 122, 132, etc.) of all of the PSUs (e.g., PSUs 110, 120, 130, etc.) of a sanitization system 100. Since the sanitization apparatuses (113, 123, 133) utilize a light source having a wavelength between 414 nm and 474 nm, significantly less power may be utilized during a sanitization process as disclosed further herein. In this regard, the power source 108 may be kept similar to a typical power source 108 for an aircraft cabin control system, in accordance with various embodiments.

In various embodiments there may be a single sensor or a plurality of sensors for each PSU. For example, sensor(s) (e.g., sensor(s) 114, 124, 134) may each include a microphone array, an occupancy sensor, a manual trigger, or a combination thereof. In this regard, the sanitization system 100 may be configured to detect occupancy and/or configured to detect an event where cleaning may be desired, such as a detecting a sneeze, a cough, or the like.

In various embodiments, each sanitization apparatus (e.g., sanitization apparatus 113, 123, 133) may be connected via digital communications, discrete communications, or wireless communications to a respective local controller (e.g., controllers 111, 121, 131). In various embodiments, a respective local controller may be configured to monitor a health of a respective sanitizer, as well as a life of a respective sanitization apparatus. For example, controller 111 may be configured to receive light source life data from the sanitization apparatus 113, each PSU (e.g., PSUs 110, 120, 130) may be configured to track a total dosage of FAR-UV supplied to a given area. For example, the controller 111 of PSU 110 may receive a duration that sanitization apparatus 113 has been in operation and limit operation when a threshold dosage is being approached.

Figure 3A:
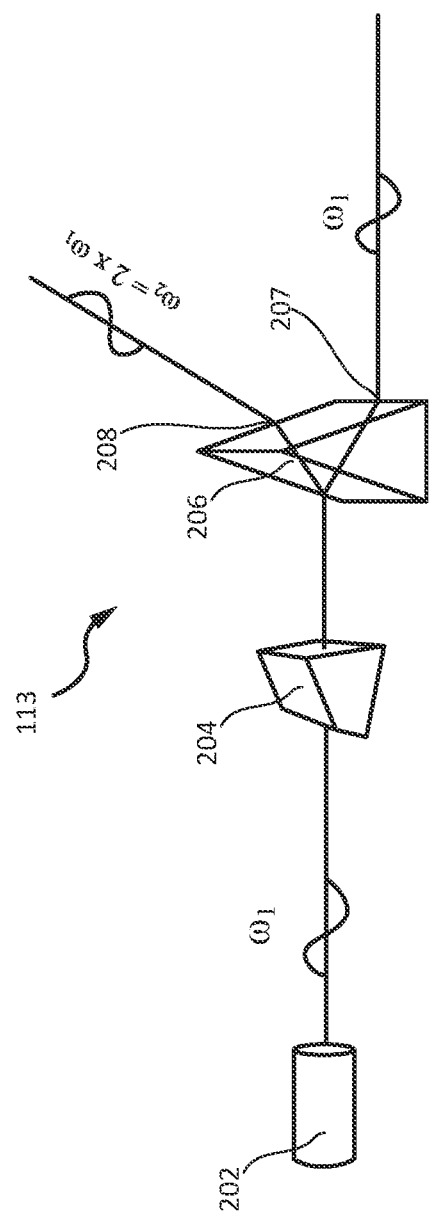
FIG. 3A illustrates a schematic view of a sanitization apparatus, in accordance with various embodiments.

Referring now to FIG. 3A, a schematic view of the sanitization apparatus 113 from FIG. 2, in accordance with various embodiments. In various embodiments, the sanitization apparatus 113 comprises a light source 202. In various embodiments, the light source 202 may comprise a light emitting diode (LED), a Nd:YAG/LBO laser, a InGaN laser diode, an InGaN laser pump source or the like. In various embodiments, any light source capable of generating a light with a first wavelength (i.e., input wavelength or pump wavelength) between 414 nm and 474 nm is within the scope of this disclosure. In various embodiments, the light source may weigh significantly less than a light source capable of generating a UVC wavelength (e.g., between 200 nm and 280 nm). In various embodiments, the light source 202 is in operable communication with a controller (e.g., a local controller 111 from FIG. 1 and/or a main controller 102). In this regard, in response to receiving a signal from a controller, the light source 202 may be activated and generate a wavelength between 414 nm and 474 nm, or between 429 and 459 nm, or approximately 444 nm.

In various embodiments, the sanitization apparatus 113 further comprises a nonlinear converter 204. The nonlinear converter 204 is configured to double a frequency of a portion of an incoming light, in accordance with various embodiments. In various embodiments, the nonlinear converter 204 is configured for second harmonic generation (SHG). Phase matching may be used in nonlinear crystals for efficient nonlinear interaction between electromagnetic waves with different wavelengths. Several strategies are utilized for nonlinear phase matching in bulk crystal (e.g., birefringent phase matching, angle phase matching, and/or quasi-phase matching).

In various embodiments, materials with a refractive index near zero may tend to provide a phase-mismatch-free environment for nonlinear optical processes and may be disruptive for nonlinear conversion, as described further herein. In various embodiments, index near zero material may be supported with cavities or single-back reflectors to increase an optical path.

Figure 3B:
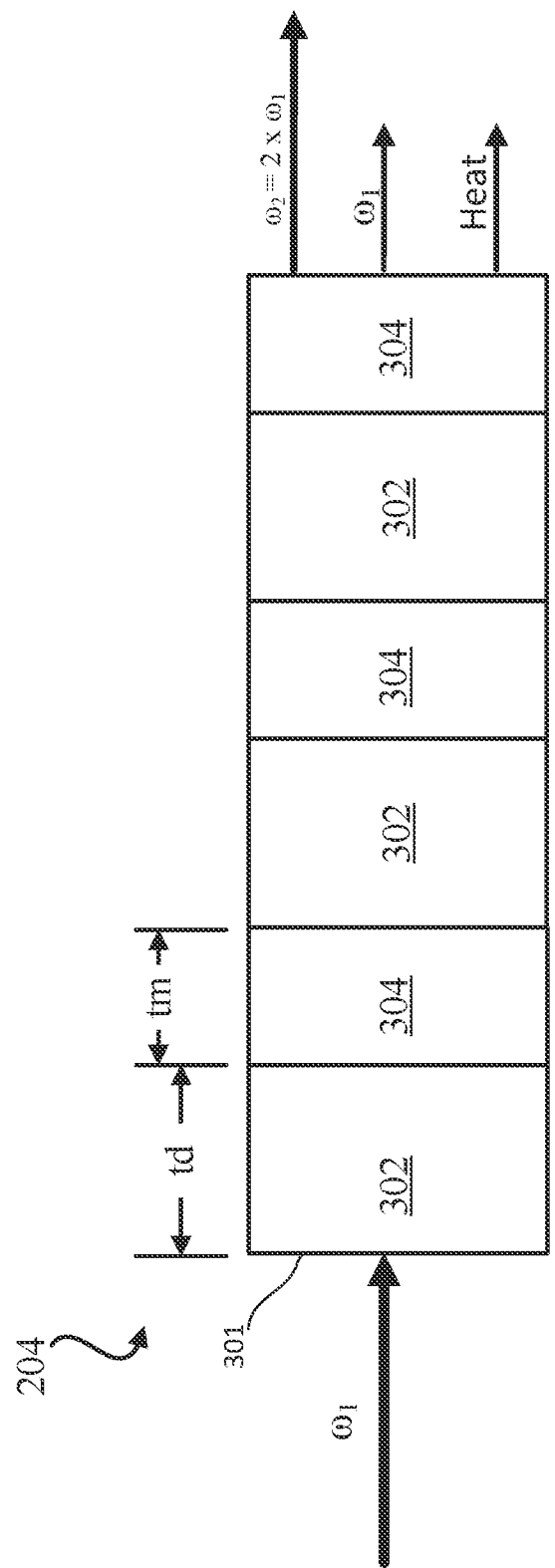
FIG. 3B illustrates a schematic view of a nonlinear converter, in accordance with various embodiments.

With brief reference now to FIG. 3B, a nonlinear converter 204 in accordance with various embodiments, is illustrated. The nonlinear converter 204 may comprise alternating layers of a dielectric material 302 and a metallic material 304. The nonlinear converter 204 is configured with a refractive index near zero. A "near zero" refractive index as described herein refers to a refractive index between 0 and 1, or between 0 and 0.75, or between 0 and 0.5, or between 0 and 0.3. In various embodiments, both the real portion and the imaginary portion of index are near zero. In this regard, the real part of the refractive index being near zero facilitates a phase mismatch-free medium as described previously herein. The imaginary part of the refractive index being near zero may minimize optical losses.

Although illustrated as comprising alternating layers of the dielectric material 302 and the metallic material 304, the present disclosure is not limited in this regard. For example, one skilled in the art may recognize various orientations or configurations to produce a near zero refractive index material that provides nonlinear conversion properties as outlined herein. In this regard, any nonlinear converter configured to receive a first wavelength of light (i.e., an input wavelength or a pump wavelength) and output a second wavelength of light (i.e., an output wavelength or SHG wavelength) with a near zero refractive index for the first wavelength of light and the second wavelength of light is within the scope of this disclosure.

In various embodiments, the dielectric material 302 comprises a thickness to and the metallic material 304 comprises a thickness $t_m$. The thicknesses td, $t_m$ are measure in an axial direction of the nonlinear converter (i.e., perpendicular to a first axial surface 301 defining an inlet for an incoming light), in accordance with various embodiments.

In various embodiments, the dielectric material 302 includes a refractive index, nd and the metal material includes a refractive index, $n_m$. The refractive index, $n_d$ is a function of the fill ratio. Fill ratio is a function of the thickness, $t_m$, of the metal material 304 and the thickness, $t_d$, of the dielectric material. In particular, fill ratio ($f_m$) is defined by the following equation:

$$f_m = \frac{t_m}{t_m + t_d} \quad (1)$$

Additionally, a refractive index is a function of metal fill ratio for various wavelengths of light. For example, with reference now to FIG. 4, a plot of refractive index as a function of fill ratio for a metal material (e.g., aluminum) and a dielectric material (e.g., aluminum, nitride) for a first wavelength (i.e., input wavelength or pump wavelength) (444 nm) and a second wavelength (i.e., output wavelength or second harmonic generation (SHG) wavelength) (222 nm) are illustrated. In various embodiments, based on the plot from FIG. 4, a metal fill ratio for the nonlinear converter 204 may be determined as described further herein.

In various embodiments, the metal fill ratio for the nonlinear converter 204 may be determined based on matching a frequency of a first wavelength (e.g., a fundamental wavelength) of an input light with a second wavelength (i.e., output wavelength or second harmonic generation (SHG) wavelength) output from the nonlinear converter (e.g., a second harmonic generation wavelength). For example, a wavelength through the nonlinear converter 204 is defined by the following equation:

$$\lambda = \frac{\lambda_0}{n} \quad (2)$$

Figure 4:
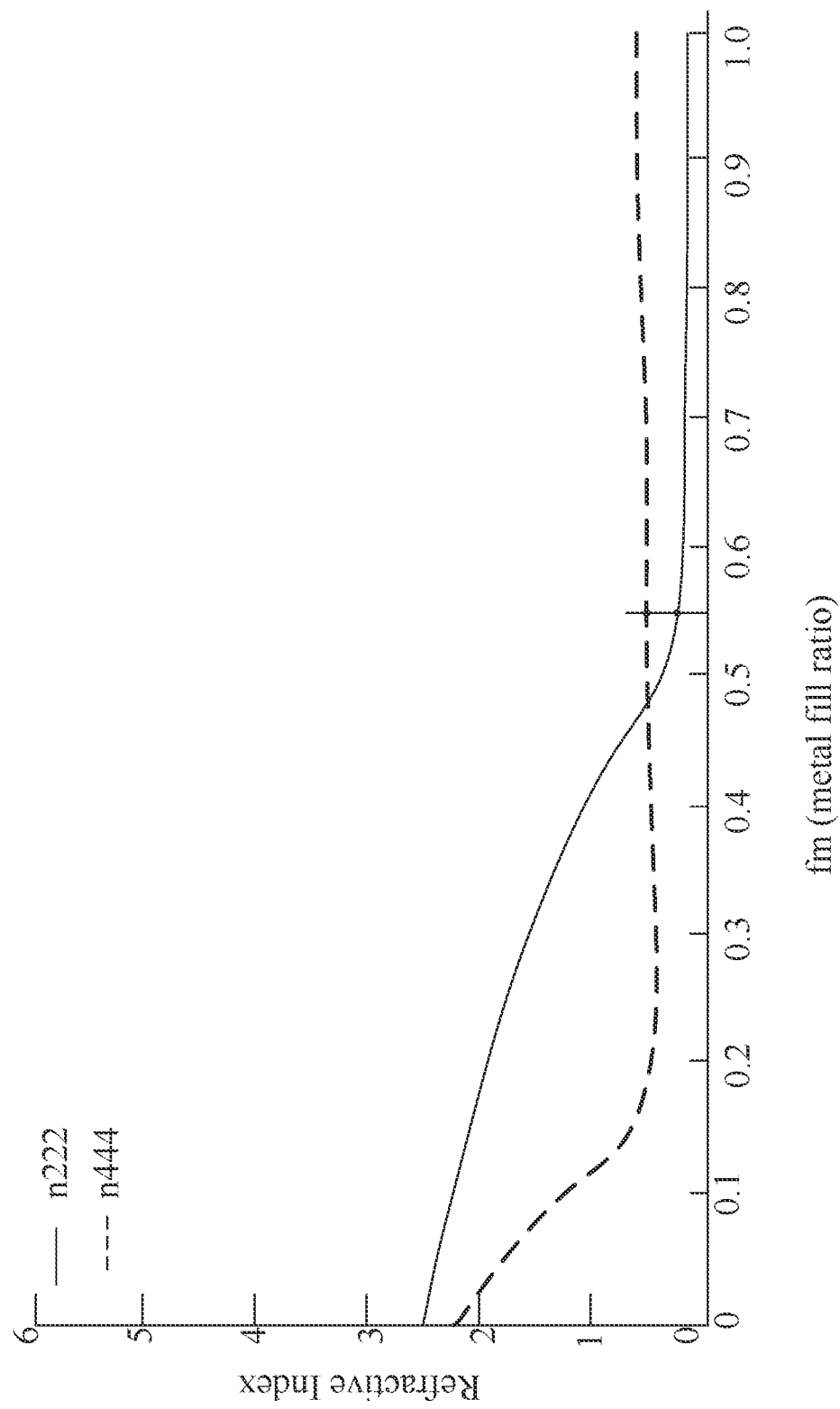
FIG. 4 illustrates a plot of refractive index vs. fill ratio for a nonlinear converter, in accordance with various embodiments.

In various embodiments, a fill ratio from the plot in FIG. 4 may be determined based on minimizing the refractive index for the first wavelength (i.e., input wavelength or pump wavelength) and the second wavelength (i.e., output wavelength or second harmonic generation (SHG) wavelength), based on having a refractive index below 1, where the refractive index of a the first wavelength (e.g., a fundamental wavelength of the input light or pump light) is approximately double a refractive index of a second wavelength (i.e., output wavelength or SHG wavelength). "Approximately double" as referred to herein, is between 1.8 and 2.2 times, or between 1.9 and 2.1 times, or between 1.95 and 2.05 times, in accordance with various embodiments. For example, for a metal material 304 comprising aluminum and a dielectric material 302 comprising aluminum nitride a fill ratio of 0.55 may have a refractive index for a first wavelength (i.e., input wavelength or pump wavelength) of 444 nm of approximately 0.487 and a refractive index of a second wavelength (i.e., output wavelength or SHG wavelength) of 222 nm of approximately 0.236.

Thus, a wavelength through the nonlinear converter 204 for a first wavelength (i.e., input wavelength or pump wavelength) of 444 nm having a refractive index of 0.487 would be approximately 911 nm. Similarly, a wavelength through the nonlinear converter 204 for a second wavelength (i.e., output wavelength or SHG wavelength) of 222 nm corresponding to the second harmonic generation would be approximately 941.5. Thus, a mismatch between the first wavelength (i.e., input wavelength or pump wavelength) and the second wavelength (i.e., output wavelength or SHG wavelength) through the nonlinear converter would be defined by the following equation:

$$\text{Mismatch} = \frac{|\lambda_{SHG} - \lambda_f|}{\lambda_f} \quad (3)$$

where $\lambda_{SHG}$ is the second harmonic generation wavelength through the nonlinear converter 204, and $\lambda_f$ is the fundamental frequency through the nonlinear converter 204. Thus, in the example above, the mismatch would be approximately 3.3%.

Figure 5:
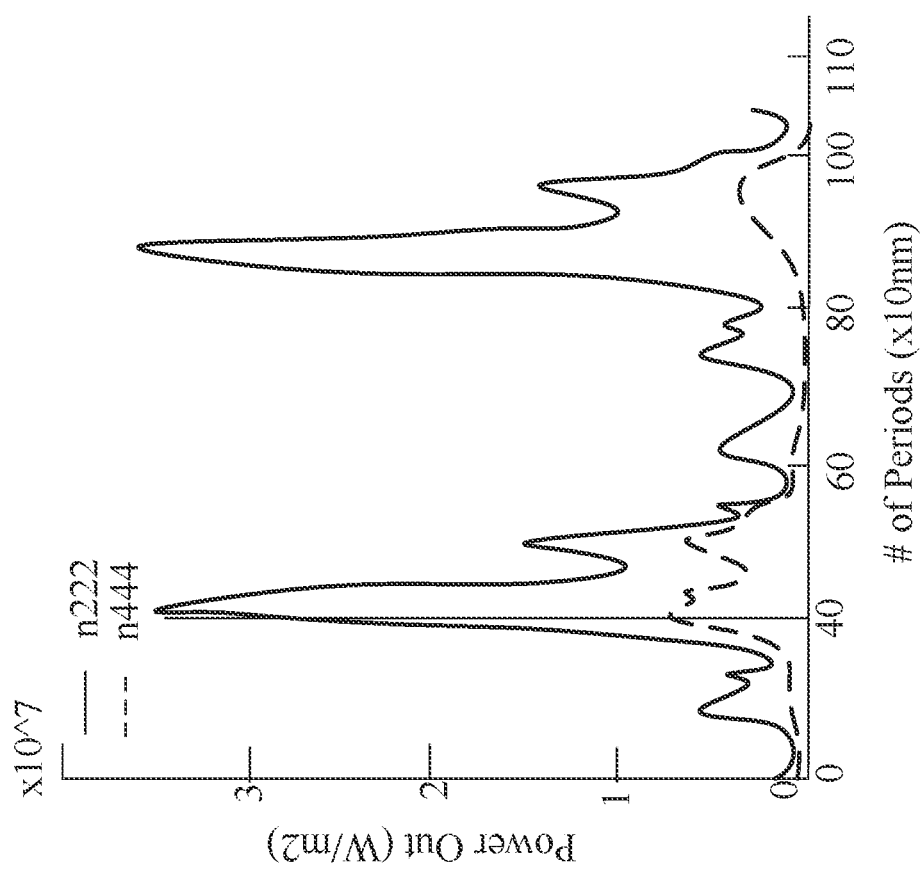
FIG. 5 illustrates a plot of power vs. nonlinear converter thickness, in accordance with various embodiments.

In various embodiments, after having a fill ratio resulting in a low mismatch between wavelengths (e.g., between 0% and 20% mismatch, or between 0% and 10% mismatch, or between 0% and 5% mismatch), a thickness of the metal material 304 and the dielectric material 302 may be determined. Power output may be a function of number of periods through a material. For example, with reference to FIG. 5, power output of a metal material 304 comprising aluminum and a dielectric material 302 comprising aluminum nitride is illustrated for a first wavelength (i.e., input wavelength or pump wavelength) of light at approximately 444 nm and a second wavelength (i.e., output wavelength or SHG wavelength) of light at approximately 222 nm. In this regard, a power output of the second wavelength (i.e., output wavelength or SHG wavelength) (e.g., 222 nm) may be maximized, a power output of the first wavelength (i.e., input wavelength or pump wavelength) (e.g., 444 nm) may be maximized, or power output of both the first wavelength (i.e., input wavelength or pump wavelength) and the second wavelength (i.e., output wavelength or SHG wavelength) may be determined with the goal of maximizing both power outputs, in accordance with various embodiments.

In various embodiments, determining a compositing for a nonlinear converter 204 as described herein may comprise balancing the following factors: (1) maximizing power output of the second wavelength (i.e., output wavelength or SHG wavelength) (e.g., approximately 222 nm wavelength light); (2) minimizing a refractive index of the second wavelength (i.e., output wavelength or SHG wavelength); and (3) minimizing a mismatch between the first wavelength (i.e., input wavelength or pump wavelength) through the nonlinear converter and the second wavelength (i.e., output wavelength or SHG wavelength) through the nonlinear converter.

Although described herein with respect to aluminum as the metal material 304 and aluminum nitride as the dielectric material, the present disclosure is not limited in this regard. For example, any metal material and dielectric material determined in accordance with the above is within the scope of this disclosure.

In various embodiments, the nonlinear converter 204 comprises a Far-UV refractive index between 0 and 1, or between 0 and 0.5 or between 0 and 0.3. In various embodiments, a nonlinear converter 204 is configured to generate a first wavelength corresponding to an input wavelength and a second wavelength (i.e., output wavelength or SHG wavelength) corresponding to a second harmonic generation wavelength. In various embodiments the first wavelength (i.e., input wavelength or pump wavelength) and the second wavelength (i.e., output wavelength or SHG wavelength) generated within the nonlinear converter 204 are approximately equal. "Approximately equal" as defined herein refers to a mismatch of between 0% and 20% or 0% and 10% or 0% and 5%, or 0% and 3%. A metal fill ratio of the metal material 304 to the dielectric material 302 may correspond to a first refractive index of a wavelength between 414 nm and 474 nm. The metal fill ratio of the metal material 304 to the dielectric material 302 also corresponds to a second refractive index of a wavelength between 207 nm and 237 nm. In various embodiments, the first refractive index is approximately double the second refractive index.

Referring back to FIG. 3A, in various embodiments, the output from the nonlinear converter 204 is received by a prism 206 configured to direct the light received from the nonlinear crystal. For example, the first portion of the light with the first wavelength (i.e., input wavelength or pump wavelength) may directed through first output 207 of the prism 206 and the second portion of the light with the second wavelength (i.e., output wavelength or SHG wavelength) may be directed through a second output 208. In various embodiments, the first output and the second output may be collimated (i.e., parallel or the like). In this regard, the first wavelength (i.e., input wavelength or pump wavelength) may indicate to a person that the area is being sanitized as the first wavelength (i.e., input wavelength or pump wavelength) would have greater visibility relative to the second wavelength (i.e., output wavelength or SHG wavelength), in accordance with various embodiments. Although illustrated as being separated, the first wavelength (i.e., input wavelength or pump wavelength) and the second wavelength (i.e., output wavelength or SHG wavelength) may be coaxial in accordance with various embodiments. In this regard, the first wavelength (i.e., input wavelength or pump wavelength) may indicate more clearly a location being sanitized, in accordance with various embodiments. Additionally, in various embodiments, the residual light of the first wavelength (i.e., input wavelength or pump wavelength) through first output 207 may be mixed with an additional light source (e.g., light(s) 112 from FIG. 2) to create white light, such as for use as a reading light or the like. Although described with respect to sanitization apparatus 113, any sanitization apparatus disclosed herein (e.g., sanitization apparatuses 123, 133) may be in accordance with sanitization apparatus 113 from FIG. 3, in accordance with various embodiments.

Figure 6:
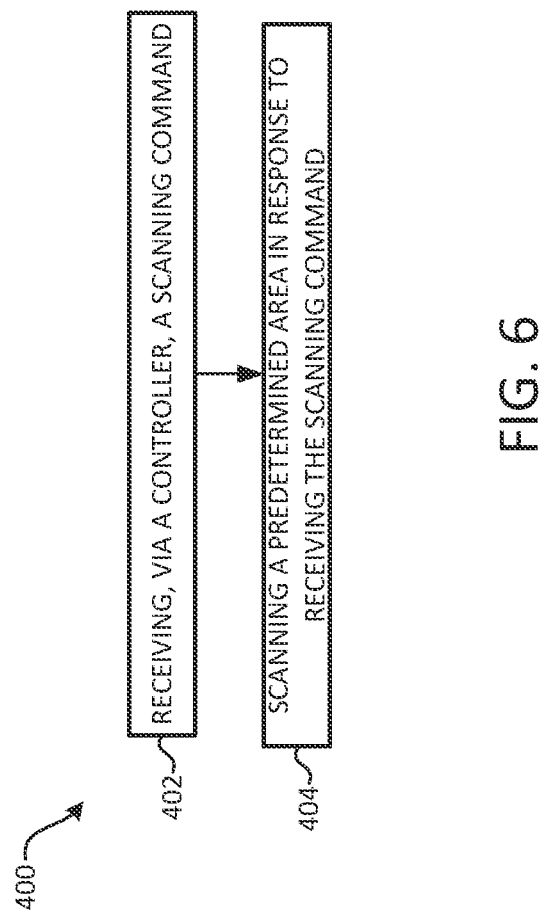
FIG. 6 is a process performed by a control system for a sanitization system, in accordance with various embodiments.

Referring now to FIG. 6, a method of sanitization a portion of an aircraft is illustrated, in accordance with various embodiments. The method may comprise receiving, via a controller, a scanning command (step 402). The scanning command may include a predefined area. In various embodiments, since the output from the prism of 206 of the sanitization apparatus 113 is a beam, it can be directed in a manner similar to a barcode scanner or the like. In contrast, excimer lamps, and other far-UV light sources cannot generate a beam of light that can be directed. Thus, the systems and methods disclosed herein may facilitate scanning areas and avoiding people when sanitizing a particular area. In this regard, sensor(s) 114, 124, 134 from FIG. 2 may include infrared sensors, LiDAR sensors, or the like. The sensors may be configured to detect and identify people, and the controller (e.g., main controller 102 or local controllers 111, 121, 131) may be configured to command the sanitization apparatus to direct the output beam(s) away from people, in accordance with various embodiments.

The method 400 may further comprise scanning a predetermined area in response to receiving the scanning command (step 404). In various embodiments, the predetermined area may be an area that commonly comes into contact with passengers, such as tray tables, arm rests, or the like. In various embodiments, scanning the predetermined area may be an active scanning where portions of the area are avoided in response to detecting a person as described previously herein.

Figure 7:
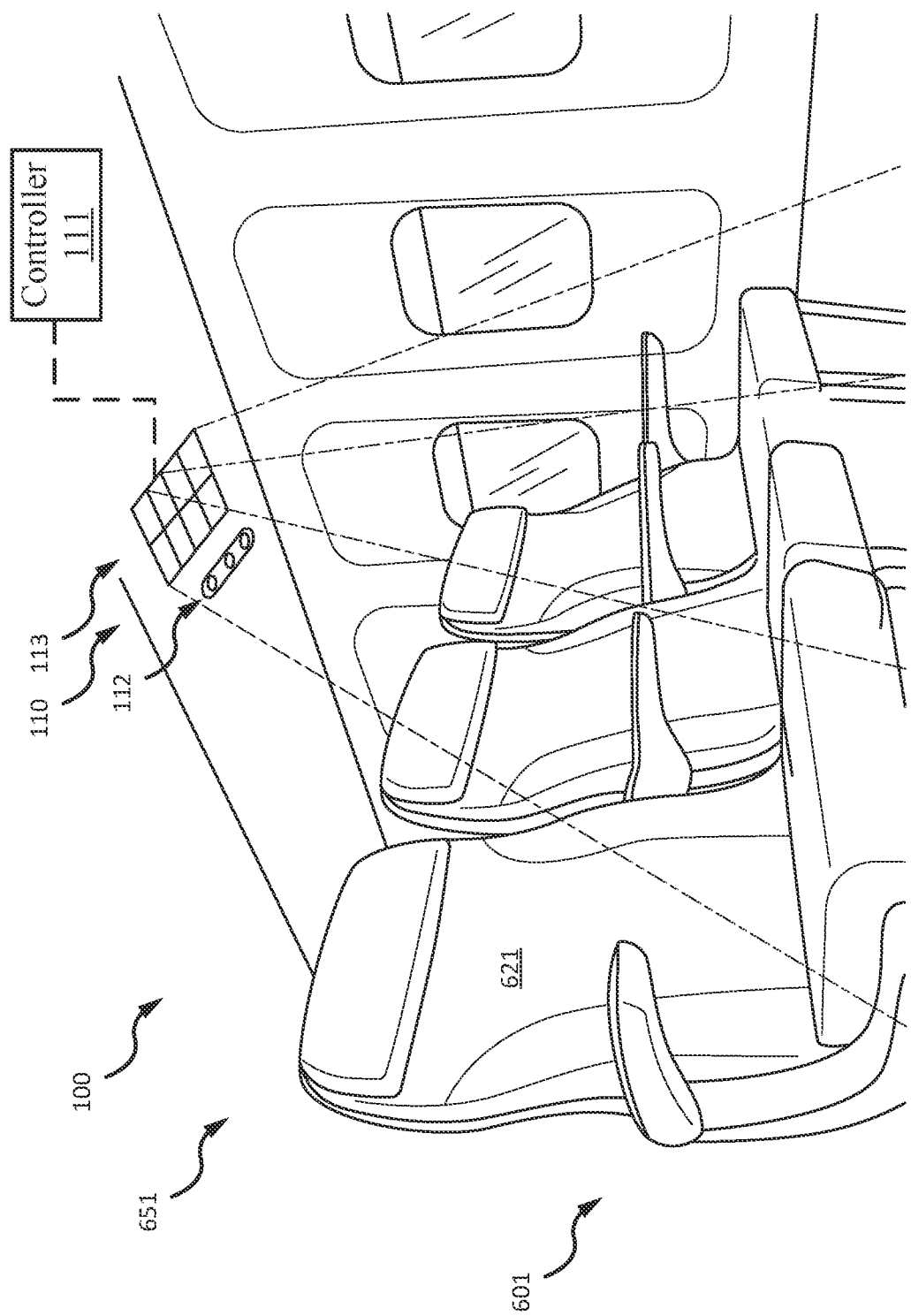
FIG. 7 is a perspective view of a portion of a sanitization system 100, in accordance with various embodiments.

Referring now to FIG. 7, a perspective view of a portion of the sanitization system 100 from FIG. 2 is illustrated, in accordance with various embodiments. The sanitization system 100 includes the light(s) 112 and the sanitization apparatus 113. In various embodiments, each light(s) 112 may correspond to a seat in a respective row. For example, a first light 611 may be configured to align towards a first seat 621 in a row 601 of in the aircraft cabin 651. In this regard, each light in the light(s) 112 in a PSU 110 may be configured to emit light towards a seat in a row of the respective PSU 110.

In various embodiments, the sanitization apparatus 113 in a PSU 110 includes the light source 202, the nonlinear converter 204, and the prism 206 from FIG. 2. Although illustrated as including a plurality of the sanitization apparatus 113, any number of sanitization apparatuses 113 for a respective PSU 110 is within the scope of this disclosure. In various embodiments, the local controller 111 (or main controller 102) from FIG. 2 may adjust a beam direction of a respective sanitization apparatus 113 during a sanitization process (e.g., method 400). In various embodiments, the sanitization system 100 may be configured to direct the light away from a passenger's head (e.g., towards the tray tables, or the like).

Figure 8:
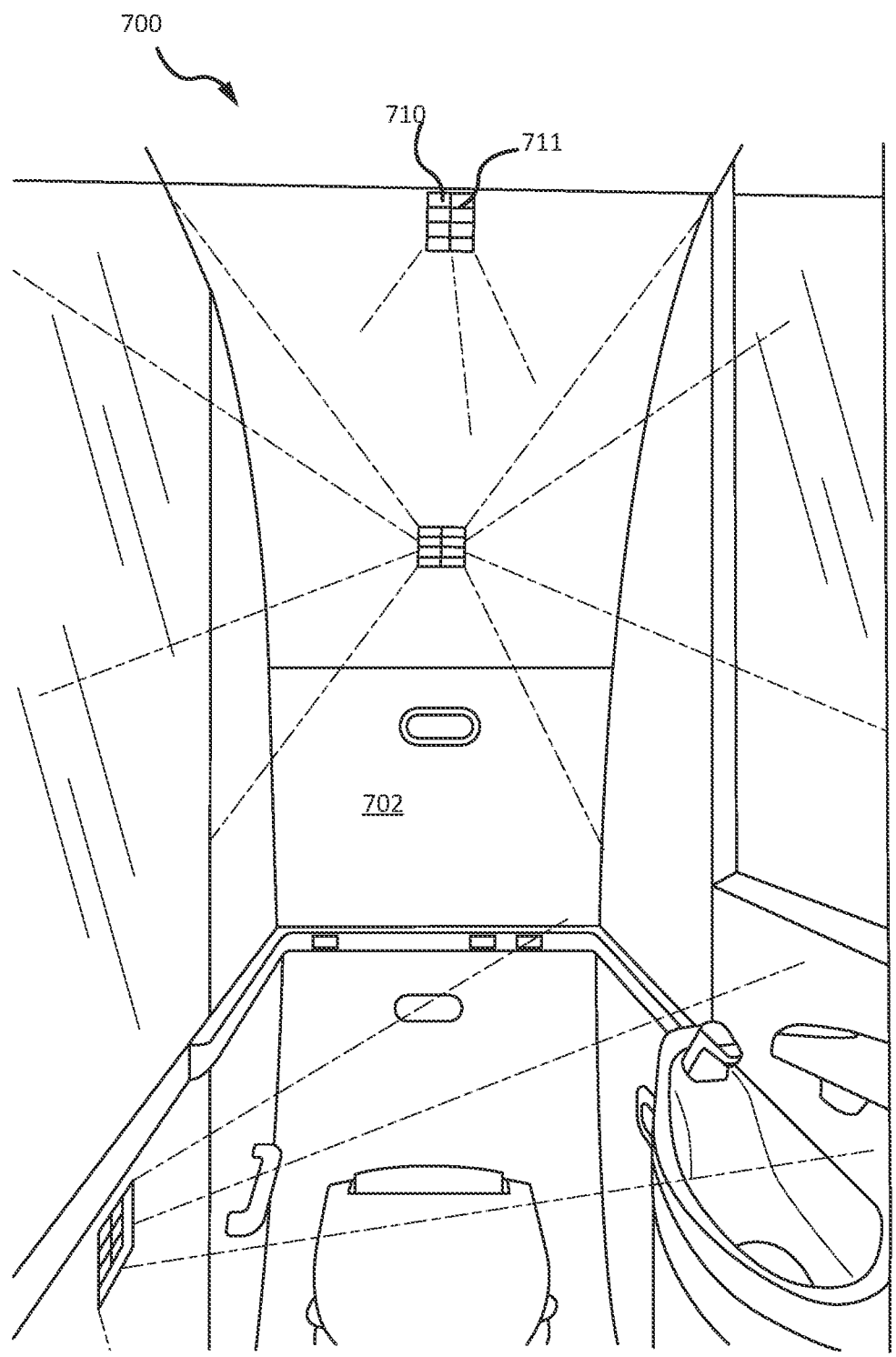
FIG. 8 is a perspective view of a lavatory in an aircraft, in accordance with various embodiments.

Referring now to FIG. 8, a perspective view of a sanitization system 700 is illustrated, in accordance with various embodiments. In various embodiments, the sanitization system 700 may be disposed in a lavatory 702 of an aircraft cabin (e.g., aircraft cabin 51 from FIG. 1). In this regard, the sanitization system 700 may be configured in a manner similar to sanitization system 100. For example, the sanitization system may include sensor(s) configured to detect whether the bathroom is occupied (e.g., sensor(s) 114 from FIG. 2), a sanitization apparatus 710 (e.g., sanitization apparatus 113), and a controller (e.g., controller 111 from FIG. 1). In various embodiments, the sanitization system 700 may be in communication with main controller 102 from the sanitization system 100 from FIG. 2. In this regard, the lavatory 702 may be configured to be sanitized during in-flight cycle, post-flight cycle, or the like. In various embodiments, the lavatory 702 may be configured to be sanitized after use (e.g., in response to detecting a user entering and detecting a user leaving).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A nonlinear converter comprising:
   alternating layers of a dielectric material and a metal material, the nonlinear converter configured to receive a first wavelength and output a second wavelength;
   a first refractive index of the nonlinear converter for the first wavelength, the first wavelength being between 414 nm and 474 nm, the first refractive index corresponding to a metal fill ratio; and
   a second refractive index of the nonlinear converter for the second wavelength, the second wavelength being between 207 nm and 237 nm, the second refractive index between 0 and 0.3, the second refractive index corresponding to the metal fill ratio.

2. The nonlinear converter of claim 1, wherein at least a portion of the first wavelength is halved in response to traveling through the nonlinear converter.

3. The nonlinear converter of claim 2, wherein the first wavelength and the second wavelength are approximately equal, wherein approximately equal is between 0% and 10%.

4. The nonlinear converter of claim 3, wherein approximately equal is between 0% and 5%.

5. The nonlinear converter of claim 1, wherein the dielectric material is aluminum nitride, and wherein the metal material is aluminum.

6. The nonlinear converter of claim 1, wherein the nonlinear converter is configured to receive a first light with the first wavelength and output the first light and a second light with the second wavelength.

7. A sanitization apparatus, comprising:
   a light source configured to emit a light having a first wavelength between 414 and 474 nm; and
   a nonlinear converter disposed proximate to the light source, the nonlinear converter comprising alternating layers of a dielectric material and metal material, the nonlinear converter configured to provide a phase mismatch between an input wavelength and a second harmonic generation wavelength between 0% and 10% within the nonlinear converter, wherein:
   a first refractive index of the nonlinear converter for the second harmonic generation wavelength is less than 0.5, the first refractive index corresponding to metal fill ratio of the alternating layers, and a second refractive index of the nonlinear converter for the input wavelength is approximately double the first refractive index.

8. The sanitization apparatus of claim 7, wherein the second harmonic generation wavelength is between 207 and 237 nm.

9. The sanitization apparatus of claim 7, wherein the second refractive index corresponds to the metal fill ratio.

10. The sanitization apparatus of claim 9, wherein the nonlinear converter is configured to generate a third wavelength and fourth wavelength within traveling through the alternating layers of the dielectric material and the metal material, the third wavelength and the fourth wavelength being approximately equal.

11. The sanitization apparatus of claim 10, wherein approximately equal is between 0% and 5%.

12. A method of sanitizing a surface, comprising:
generating a light having a first wavelength between 414 and 474 nm; and
converting the light into a first portion of the light having the first wavelength and a second portion of the light having a second wavelength, the second wavelength being half the first wavelength, converting the light being through a phase-mismatch free medium, the phase-mismatch free medium including a phase mismatch between 0% and 10%, wherein converting the light further comprises generating, via a nonlinear converter, a third wavelength corresponding to the first wavelength and a fourth wavelength corresponding to the second wavelength, the third wavelength and the fourth wavelength being approximately equal.

13. The method of claim 12, further comprising directing the second portion of the light towards the surface.

14. The method of claim 13, wherein directing the second portion of the light toward the surface is through a prism.

15. The method of claim 12, further comprising directing the first portion of the light in a first direction that is collimated with a second direction of the second portion of the light.

16. The method of claim 15, further comprising scanning a predetermined area of the surface with the second portion of the light.

* * * * *